US00PP24421P2

(12) United States Plant Patent
Sidhu

(10) Patent No.: US PP24,421 P2
(45) Date of Patent: May 6, 2014

(54) ***THUJA* PLANT NAMED 'THUSID2'**

(50) Latin Name: *Thuja occidentalis*
Varietal Denomination: Thusid2

(71) Applicant: Gurjit Sidhu, Mission (CA)

(72) Inventor: Gurjit Sidhu, Mission (CA)

( * ) Notice: Subject to any disclaimer, the term of this patent is extended or adjusted under 35 U.S.C. 154(b) by 44 days.

(21) Appl. No.: 13/573,955

(22) Filed: Oct. 16, 2012

(51) Int. Cl.
*A01H 5/00* (2006.01)

(52) U.S. Cl.
USPC ..... Plt./213

(58) Field of Classification Search
USPC ..... Plt./213
See application file for complete search history.

*Primary Examiner* — Kent L Bell
(74) *Attorney, Agent, or Firm* — Penny J. Aguirre

(57) ABSTRACT

A new cultivar of *Thuja occidentalis* named 'Thusid2' characterized by its foliage with bright yellow-green new growth from the base to the tips of the foliage, its coarse textured foliage, and its narrowly upright semi-compact plant habit.

2 Drawing Sheets

Botanical classification: *Thuja occidentalis*.
Varietal denomination: 'Thusid2'.

BACKGROUND OF THE INVENTION

The present invention relates to a new and distinct cultivar of *Thuja occidentalis* and will be referred to hereafter by its cultivar name, 'Thusid2'. 'Thusid2' represents a new western red cedar, an evergreen tree grown for landscape use.

The inventor discovered this new *Thuja* (un-patented) as a naturally occurring branch mutation of *Thuja occidentalis* 'Brandon' (not patented) in spring of 2007 that was growing in a container block at his nursery in Mission, B.C., Canada.

Asexual reproduction of the new cultivar was first accomplished by stem cuttings in Mission, B.C., Canada in winter of 2007 by the inventor. Further generations of cuttings were taken in following years and trials have determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'Thusid2', as unique from all other selections and forms of *Thuja occidentalis* known to the inventor.

1. 'Thusid2' exhibits foliage with bright yellow-green new growth from the base to the tips of the foliage.
2. 'Thusid2' exhibits coarse textured foliage.
3. 'Thusid2' exhibits a narrowly upright semi-compact plant habit.

'Brandon', the parent plant of 'Thusid2', differs from 'Thusid2' in having new growth that is green in color. 'Thusid2' can be most closely compared to other cultivars of *Thuja occidentalis* that exhibit yellow-green colored foliage: 'Thusid1' (U.S. Plant Pat. No. 22,003), 'Golden Brabant' (U.S. Plant patent application Ser. No. 13/507,129), and 'Golden Anne' (U.S. Plant patent application Ser. No. 13/506,864). 'Thusid1' differs from 'Thusid2' in having yellow color only on the tips of the new growth, in having finer textured foliage, and in having a more compact, dense plant habit.

'Golden Brabant' differs from 'Thusid2' in having foliage that is yellow in color on mature foliage as well as new foliage and in having a more ovate to conical plant habit. 'Golden Anne' differs from 'Thusid2' in having foliage that is yellow in color on mature foliage as well as new foliage and in having a broader plant habit.

BRIEF DESCRIPTION OF THE DRAWING

The plant and plant parts depicted in the accompanied photographs illustrate the characteristics of 'Thusid2'. The photographs were taken of three year-old plants as grown outdoors in two-gallon containers in Mission, B.C., Canada.

Figure 1:
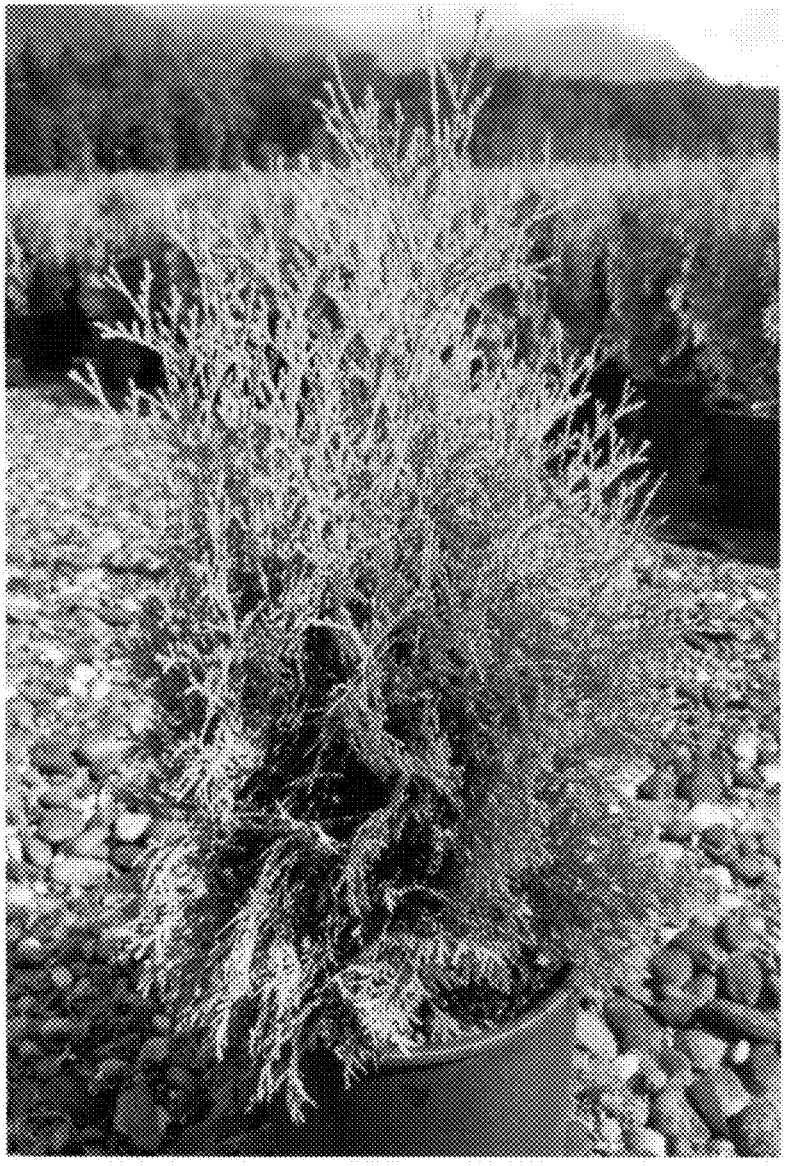
FIG. 1 provides an overall view of the plant habit of 'Thusid2'.
Figure 2:
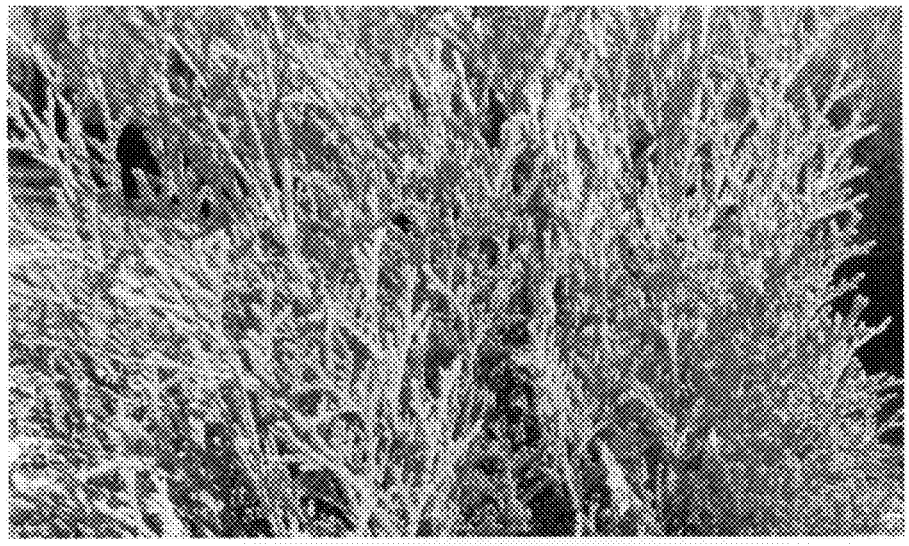
FIG. 2 provides a close-up view of the foliage of 'Thusid2'.
Figure 3:
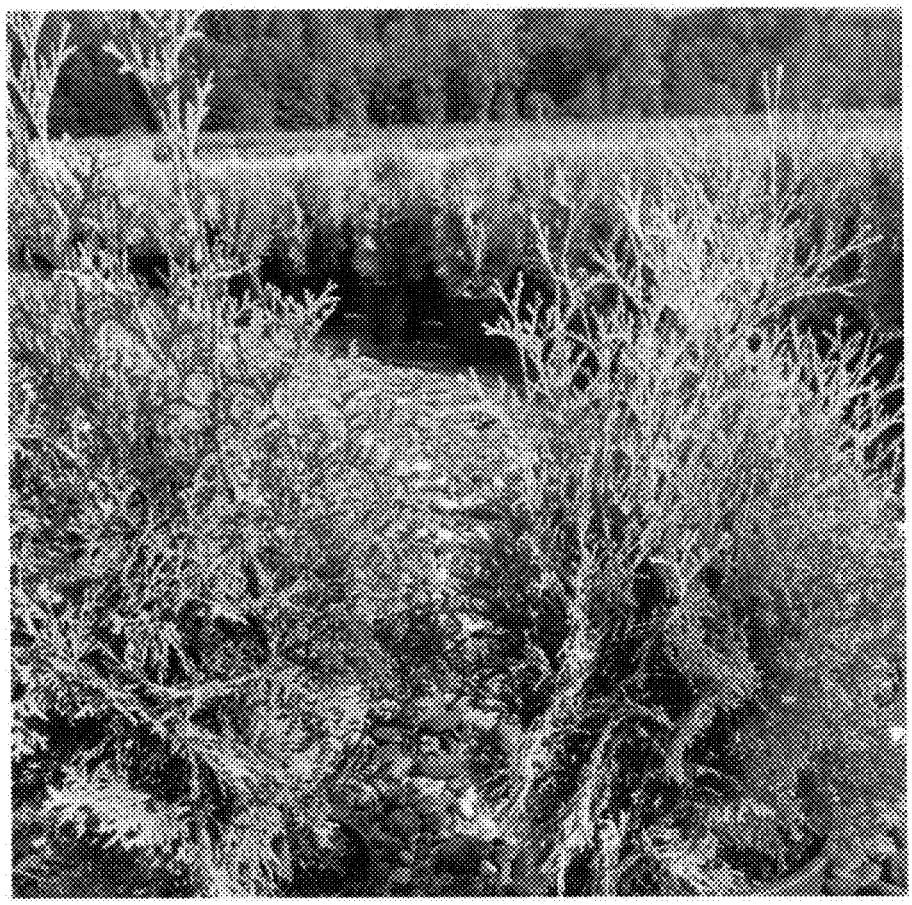
FIG. 3 provides a view of 'Thusid2' (right) in comparison to 'Brandon' (left).

The colors in the photographs are as close as possible with the photographic and printing technology utilized. The color values cited in the detailed botanical description accurately describe the colors of the new *Thuja*.

DETAILED BOTANICAL DESCRIPTION

The following is a detailed description of the new cultivar of two year-old plants of the new cultivar as grown in one-gallon containers in Mission, B.C., Canada. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type.*—Coniferous, evergreen, tree for landscape use.

*Growth habit.*—Narrowly upright, semi-compact with coarse foliage.

*Height and spread.*—An average of 21 cm in height and 12 cm in width as grown in a one-gallon container, reaches up to 4.5 m in height and 2 m in width in the landscape.

*Cone development.*—Neither male nor female cones have been observed.

*Cold hardiness.*—U.S.D.A. Zone 3.

*Diseases and pests.*—No susceptibility or resistance to diseases or pests known to affect *Thuja* has been observed.

*Root description.*—Fibrous.

*Growth rate.*—Moderate.

*Propagation.*—Stem cuttings.

Stem description:

*Shape.*—Rounded.

*Stem size.*—Main branches: average of two main branches, 1 cm in diameter and 37 cm in length; lateral branches: average of 4 mm in diameter and 14 cm in length.

*Stem surface.*—Young branches are glabrous and knobby with scales.

*Branching.*—Main stems arise from base with numerous secondary branches, number of lateral branches an average of 10 per main branch.

*Branch arrangement.*—Alternate.

*Branch aspect.*—Main stems upright, lateral stems held at an average angle of 10° from the main stems with flat sprays that spread upward and outward.

*Internode length.*—Range from 3.5 cm at the base to 2.5 cm at the tip.

*Stem color.*—Immature branches are 166A with scales 167D, mature branches are 200A with scales 165D in color.

Foliage description:

*Leaf arrangement.*—Numerous leaves arranged on planar branchlets scale-like decussate.

*Leaf shape.*—Facial pair keeled, flat pair flattened and oblong.

*Leaf division.*—Simple.

*Leaf base.*—Cuneate.

*Leaf apex.*—Apiculate.

*Leaf venation.*—Not visible.

*Leaf margins.*—Entire.

*Leaf surface.*—Upper and lower; scale like, glabrous, dull.

*Leaf color.*—Mature upper surface: between a blend of 147A and 143B; mature lower surface: 143A; new growth upper and lower surface; 154B to 154C in color.

*Leaf fragrance.*—Evergreen scent when crushed.

*Leaf size.*—An average of 4 cm in length and 1 cm in width.

*Leaf quantity.*—About 5 per lateral branch.

Cone description: No cones have been observed on the plants trialed for data collection.

It is claimed:

1. A new and distinct cultivar of *Thuja* plant named 'Thusid2' as herein illustrated and described.

* * * * *